(12) United States Patent
Esch

(10) Patent No.: US 8,491,909 B2
(45) Date of Patent: Jul. 23, 2013

(54) METHODS AND COMPOSITIONS FOR DOSING OF ALLERGENS

(75) Inventor: Robert E. Esch, Lenoir, NC (US)

(73) Assignee: Greer Laboratories, Inc., Lenoir, NC (US)

( * ) Notice: Subject to any disclaimer, the term of this patent is extended or adjusted under 35 U.S.C. 154(b) by 596 days.

(21) Appl. No.: 11/052,577

(22) Filed: Feb. 7, 2005

(65) Prior Publication Data

US 2005/0175638 A1 Aug. 11, 2005

Related U.S. Application Data

(60) Provisional application No. 60/542,147, filed on Feb. 6, 2004.

(51) Int. Cl.
| | | |
|---|---|---|
| *A61K 39/00* | (2006.01) | |
| *A61K 39/38* | (2006.01) | |
| *A61K 39/35* | (2006.01) | |
| *A61K 39/36* | (2006.01) | |
| *A61K 39/12* | (2006.01) | |
| *A61K 35/64* | (2006.01) | |

(52) U.S. Cl.
USPC ............. 424/184.1; 424/195; 424/275.1; 424/520; 424/538

(58) Field of Classification Search
None
See application file for complete search history.

(56) References Cited

U.S. PATENT DOCUMENTS

| | | | |
|---|---|---|---|
| 4,822,611 A | 4/1989 | Booren | |
| 6,451,324 B1 | 9/2002 | Singh et al. | |
| 2004/0166123 A1* | 8/2004 | Jacobi et al. | 424/275.1 |

FOREIGN PATENT DOCUMENTS

| | | |
|---|---|---|
| EP | 1269837 | 1/2003 |
| WO | WO 94/27634 | 12/1994 |
| WO | WO 98/21951 | 5/1998 |
| WO | WO 01/56611 | 8/2001 |
| WO | WO 2004/047794 A2 * | 6/2004 |
| WO | WO 2005/077410 | 8/2005 |

OTHER PUBLICATIONS

Taudorf et al. Oral administration of grass pollen to hay fever patients. An efficacy study in oral hyposensitization. Allergy. 40(5):321-335, 1985.*

Canonica et al. 'Noninjection routes for immunotherapy.' Curr. Rev. Allerg. Immunol. 111(3):437-448, 2003.*

Leng et al. 'A double-blind trial of oral immunotherpay for Artemisia pollen asthma with evaluation of bronchial response to the pollen allergsn and serum-specific IgE antibody.' Ann. Allergy Asthma Immunol. 64:27-31, 1990.*

Black et al. 'Treatment of respiratory allergy in children by oral administration of dust and pollen extracts.' J. Allergy 21(2):148-152, 1950.*

Avian Health Network Newsletter, vol. II, Issue XI, Aug. 2004. http:llwww.stoppdd.orglhappeningslnewsletter_work104 08 news.html.*

Lillehoj et al. 'Recent Progress on the Cytokine Regulation of Intestinal Immune Responses to Eimeria.' Poultry Science. 83:611-623, 2004.*

Liliehoj et al. 'Host immunity and Vaccine Development to *Coccidia* and *Salmonella* Infections in Chickens.' J. Poultry Science. 40:151-193, 2003.*

Bischoff et al. 'Role of mast cells in allergic and non-allergic immune responses: comparison of human and murine data.' Nature Rev. 7:93-104, 2007.*

Kurucz et al. 'Current Animal Models of Bronchial Asthma.' Curr. Pharm. Des. 12:3175-3194, 2006.*

Cox et al. 'Sublingual immunotherapy: a comprehensive review.' J. Allergy Clin. Immunol. 117(5):1021-1035, 2006.*

Pradalier et al. 'Sublingual swallow immunotherapy (SLIT) with a standardized five grass pollen extract (drops and sublingual tablets) versus placebo in seasonal rhinittis.' Allergy 54(8):819-828, 2001.*

Quirino et al. 'Sublingual versus injective immunotherapy in grass pollen allergic patients: a double blind (double dummy) study.' Clin. Exp. Allergy. 26:1253-1261, 1996.*

Feliziano et al. 'Safety and efficacy of sublingual rush immunotherapy with grass allergen extracts. A double blind study.' Allergol. Immunopathol. 23(5):224-230, 1995.*

Package Insert. *Allergenic Extracts: Short Ragweed and G.S. Ragweed Mix—Suggested Dosage Schedule and Instructions*. Feb. 2005 (revised); Greer Laboratories, Inc., Lenoir, NC.

Package Leaflet for Patient. *Staloral*. Nov. 2001 (revised); Stallergenes S.A. Antony, France.

* cited by examiner

*Primary Examiner* — Nora Rooney
(74) *Attorney, Agent, or Firm* — Ballard Spahr LLP

(57) ABSTRACT

The present invention comprises methods and compositions for immunotherapy. An aspect of the invention comprises administration of one or more allergens in compositions via oral and sublingual routes. Allergen compositions are administered in dosing intervals wherein the increase in the one or more allergens administered to the patient are provided in increasing volumes of a single concentration of at least one allergen.

18 Claims, No Drawings

METHODS AND COMPOSITIONS FOR DOSING OF ALLERGENS

CROSS REFERENCE TO RELATED PATENT APPLICATIONS

The present application claims the priority of U.S. Provisional Patent Application Ser. No. 60/542,147, filed Feb. 6, 2004, which is hereby incorporated in its entirety.

TECHNICAL FIELD

The present invention relates to compositions and methods of immunotherapy in organisms with immune systems. In particular, the present invention is directed to methods and compositions for providing allergenic agents.

BACKGROUND OF THE INVENTION

Approximately one in every two American humans has an allergy to some antigen, and suffers, to some extent, from the reactions of his or her body's immune system. Allergies are a reaction of the immune system to a foreign substance. People who have allergies generally have a hyper-alert immune system that reacts to a substance in the environment, called an allergen. If one's immune system does not respond to the foreign substance, the allergen, then one is not allergic to that substance.

Allergic reactions are found in all animals that have immune systems. The tendency to have allergies, or have a responsive immune system, is inherited. Offspring do not inherit allergies to the same allergens that the parents had, just that the offspring will more likely be reactive to foreign substances. When one parent is allergic, the offspring has a 50% chance of having allergies. That risk jumps to 75% if both parents have allergies.

Allergies can be seasonal or year-round and include reactions caused by pollen, mold, insects, insect bites or stings, animal hair and dander, dust mites and other common substances in the environment. If the allergen is in the environment, such as air, surfaces, food or drink, and then contacts the human or animal, the immune system of the human or animal responds to the allergen. The body responds in a variety of ways to the allergen.

In general, when a person or animal is exposed to an allergen, a series of events takes place. The body makes a particular type of antibody, known as IgE, that has a binding particularity for the allergen. The antibodies associate with a mast cells which contain many reactions compounds, including histamine. Mast cells are found in large numbers in the airways and in the GI tract, areas where allergens can enter the body. Once the allergen is bound by the IgE on the mast cell, the mast cell is triggered to release its reactive compounds, particularly histamine, which may cause the itchiness or runny nose associated with allergic reactions.

The point of entry of the allergen into the body may decide the type of reaction that the immune system produces. If the allergen is in the air, the symptoms of the allergic reactions will include reactions in the eyes, nose and lungs. If the allergen enters through the gastrointestinal tract, the reactions will occur in the mouth, stomach and intestines. Sometimes there are systemic responses that occur regardless of the entry point of the allergen. Such responses include hives, decreased blood pressure, anaphylactic shock, or loss of consciousness. Responses to allergens may be mild, annoying or life-threatening.

Pharmaceutical agents, prescription or over-the-counter, are often used to treat the symptoms and stop the secondary effects of mast cell release, and include widely used agents such as antihistamines, inhaled steroids, nasal decongestants and cromolyn. Another approach to treatment of allergic reactions is immunotherapy, which is most frequently administered as injections, and is known as allergy shots. Allergy shots, as currently administered into the subcutaneous region of the forearm are an effective method of long-term relief from allergy symptoms. Patients are given the allergen in increasing doses until the body no longer responds in an allergic reaction to the allergen in the environment.

Many humans or animals with allergies do not get immunotherapy. Most treat the symptoms with pharmaceutical agents, just suffer through the seasons of pollen, grass or mold, or get rid of the allergen source, such as a pet. Surveys have shown that two in three people with allergies would never consider getting allergy shots. An even higher number of people would not consider such a treatment for their pets or livestock. Thus, many people and animals are suffering needlessly or constantly being medicated.

There are many reasons this type of immunotherapy, allergy shots, is avoided. Pain and annoyance are probably major considerations for avoidance. The offending allergen or allergens must be identified and this is done most often by immediate hypersensitivity testing, such as scratching the skin with a panel of allergens and noting the levels of itchiness, redness and swelling of each site.

Once the allergen is identified as one which causes an allergic reaction, and allergy shots are proposed, the patient must cooperate to a large degree in participating in this treatment regimen. Before every shot is administered, for two hours prior to and two hours after the shot, the patient should not exercise or engage in vigorous activity. Exercise may stimulate increased blood flow and promote a faster release of the allergen from the allergen depot in the arm to the bloodstream and trigger a more violent response. This level of inactivity may be problematic when treating animals and children. Taking medications, such as beta-blockers or monamine oxidase inhibitor (MAOI), may interfere if treatment is needed for the response to the allergy shot.

After receiving the shot, the patient must be monitored for thirty minutes to check for intense reactions, and avoid exercise for two hours. Redness, swelling, or irritation within one inch of the site of the injection is normal. These symptoms should go away within 4 to 8 hours after receiving the shot.

This is the outlook for the patient who must visit the physician or veterinarian weekly or bi-weekly for two to four years for these injections. Again, more pain and annoyance is involved in making and attending the appointments and receiving injections. After this series of shots, most patients are placed on several years of maintenance shots. This is an expensive and time-consuming regimen for treatment of an illness that is usually not life-threatening.

There is some danger in receiving allergy shots. The shot includes the very allergen for which the patient has a known immune response. If the immune response is triggered to react in an intense manner, the patient may die from anaphylactic shock. This is one reason a series of allergy shots may take from three to five years to reach a maintenance level. If the allergen is delivered at a faster rate, resulting in larger doses of the allergen, it may be dangerous for the patient. It is not recommended for patients with heart disease or severe asthma to even receive allergy shots.

The current therapeutic regimen for providing allergen compositions for allergy shots requires careful monitoring and preparation of the compositions by or under the control of a physician or veterinarian. Currently, only subcutaneous shots are approved by the FDA. The series of shots begins with a very dilute solution of the allergen and over time, increasing amounts of the allergen are injected using solutions having higher concentrations of the allergens. It usually takes several months and may take up to 2 years to reach a maintenance dose. Patients may experience some relief within 6 months; however, if there is no benefit within 18 months, the shots are generally discontinued.

What is needed are methods and compositions for treatment of allergic reactions that are easier to administer, with less pain, and are effective for immunotherapy for the relief of allergies. Methods that do not require constant office visits or complete physician or veterinarian oversight would also be advantageous. Methods and compositions that are easily administered to humans or animals without the need for dilution calculations to provide increasing amounts of allergen to the patient are needed for more universal use and acceptance by patients with allergy.

SUMMARY OF THE INVENTION

The present invention comprises compositions and methods for immunotherapy. An aspect of the present invention comprises methods for administering compositions of allergens for allergen immunotherapy and desensitization. The methods comprise treatment regimens comprising single or multiple dosing intervals, each of which provides step-wise changes in the dose of one or more allergens that are administered over a particular time period.

In the initial dosing interval, the patient is provided with a container of an allergen composition having a particular concentration of one or more allergens. The patient administers the allergen composition via oral or sublingual routes in prescribed volumes that are modified in a step-wise fashion over the initial dosing period. For the second dosing interval, the patient may be provided with a second container of an allergen composition. The second container contains an allergen composition wherein the concentration of one or more allergens is the same as the first container used in the initial dosing interval. Again, the patient administers the allergen composition via oral or sublingual routes in prescribed volumes that are increased or decreased in a step-wise fashion over the second dosing interval. There may be one or multiple dosing intervals in a treatment regimen. The step-wise change in the amount of one or more allergens administered during a dosing interval is accomplished by step-wise increases or decreases in the delivered volume of the allergen composition of that interval.

The current state of the art requires subcutaneous injections of multiple compositions having differing concentrations of allergens that are all administered in the same volume, thus increasing the amount of allergen delivered by using compositions having increasing concentrations

DETAILED DESCRIPTION

The present invention comprises methods and compositions for immunotherapy treatments and desensitization to allergens. The methods comprise administration of one or more allergens to a human or animal that responds with an immune response, or responds in an allergic manner, to one or more of the allergens. Routes of administration include all of those known, including but not limited to, nasal, pulmonary, inhalation, mucosal, oral, sublingual, gastrointestinal, transdermal, electrophoresis, intra-rectal, intra-vaginal, and intradermal or subcutaneous injections. The compositions comprise one or more allergens, one or more of which cause an allergic reaction in a human or animal. Allergens that are immunologically similar to allergens that cause an allergic reaction in the human or animal can also be included in the compositions. An allergen may be in the form of an allergenic extract, purified native or recombinant allergen, a modified allergen, or a nucleic acid that encodes the allergen. As used herein, allergen is any material to which a human or animal with a functioning immune system can mount an immune response such as that mediated by T cells, B cells, mast cells and other cells of the body, and the term allergen can be used interchangeably with the terms immunogen, antigen, epitope, and includes fragments and whole particles.

Immunotherapy and the methods of the present invention are effective in the management of allergies, including, but not limited to, allergic asthma, allergic rhinitis, and stinging insect hypersensitivity. Food allergies can also be treated with the present invention. Allergen immunotherapy may prevent the development of asthma in children with allergic rhinitis. Evaluation of patients with allergic reactions, such as allergic rhinitis, asthma or stinging insect allergy includes a detailed history, physical examination, and laboratory tests. A definitive diagnosis often depends on the results of allergy testing, such as immediate hypersensitivity skin tests or well-performed in vitro tests for specific IgE antibody. Immediate hypersensitivity skin tests are preferred for most patients.

An aspect of the present invention comprises methods for manufacturing and administering compositions of allergens to sublingual or oral mucosal surfaces. The methods comprise treatment regimens comprising one or multiple dosing intervals, each of which provides step-wise change in the dose of one or more allergens that are administered over a particular time period. In the initial dosing interval, the patient is provided with a container of an allergen composition having a particular concentration of one or more allergens. The patient administers the allergen composition via oral or sublingual routes in prescribed volumes. For certain aspects of the invention, there may only be one dosing interval. The initial and the maintenance dose concentration may be the same concentration of one or more allergens.

For a second or subsequent dosing interval, the patient may be provided with a second container of an allergen composition. The second container contains an allergen composition wherein the concentration of one or more allergens is the same concentration as the concentration of the composition of the initial dosing interval. In other aspects of the invention, the second container may have a concentration of one or more allergens that may be increased or decreased when compared to the first container. Again, the patient administers the allergen composition via oral or sublingual routes in prescribed volumes that can be increased in a step-wise fashion over the second dosing interval. There may be one dosing interval or multiple dosing intervals in a treatment regimen. The step-wise increase or decrease in the amount of one or more allergens administered during a dosing interval is accomplished by step-wise increases or decreases in the delivered volume of the allergen composition without modifying the concentration of the allergen in the allergen composition.

An example of a method of the present invention comprises administering an allergen in increasing dosage amounts, which increases the amount of allergen administered, from a source having a uniform concentration. For example, for administration of oral drops of an allergen composition, the following administration is followed:

TABLE 1

| Source (Concentration) | Day | AM (Time) Drops | PM (Time) Drops | AU/day |
|---|---|---|---|---|
| 500 AU/ml | 1 | 1 | 1 | 50 |
| " | 2 | 1 | 2 | 75 |
| " | 3 | 2 | 2 | 100 |
| " | 4 | 3 | 3 | 150 |
| " | 5 | 4 | 4 | 200 |
| " | 6 | 5 | 5 | 250 |
| " | 7 | 8 | 8 | 400 |
| " | 8 | 10 | 10 | 500 |
| " | 9 | 10 | 10 | 500 |
| " | 10 etc. | 10 | 10 | 500 |

The above is an example of a conservative increasing dose of allergen. An example of a rush immunization schedule could start with Day 1 having 2 drops twice a day (100 AU/day), followed by a maintenance amount of 8-10 drops twice a day (400-500 AU/day) for a continuous period. The maintenance dose may be decreased, for example, in response to environmental sources of the allergen. For example, during pollen season, a maintenance dose may be decreased because of the intake of allergen from the pollen present in the air, so that the overall intake of allergen by the patient remains the same amount of allergen.

The present invention comprises methods and compositions that provide increased benefits for manufacture of allergen compositions. The use of a single concentration of an allergen composition to accomplish dose adjustments during allergen immunotherapy affords significant manufacturing advantages over the use of two or more different concentrations as is currently practiced. Production and formulation processes are simplified by eliminating the need for dilution steps and additional quality controls. Every instance of making an original concentration of an allergen solution and then several dilutions of the original concentration require additional testing and quality control measurements and oversight. Lowering the number of manipulations of the allergen composition reduces the risks associated with prescription formulation errors and helps standardize therapeutic regimens. This provides added protection and safety for the patient and lessens the risk of mistreatment.

The present invention provides for methods of making allergen compositions wherein the concentrations of one or more allergens in the allergen compositions are not altered due to treatment regimen requirements for diluted allergen amounts for the initial doses for administration to patients.

The dose of allergen administered ranges from nanograms to milligrams of allergen provided to the patient, depending on the allergen, the route of administration and the reactions of the patient's immune system. In general, for injection administration route, the starting injection immunotherapy dose is 1,000-fold to 10,000 fold less than the maintenance dose. For example, the recommended starting dose for short ragweed pollen allergen immunotherapy is 15 ng of the allergen (0.05 mL of a 0.3 μg/mL allergen solution). The dose is increased at 5 to 7 day intervals for 18 injections until reaching the maintenance dose of 15 μg of major allergen (0.5 mL of a 30 μg/mL allergen solution) and a cumulative dose of 85 μg given over a period of 3 to 4 months; see Table 2. The use of a sublingual/oral route of administration allows for significantly higher cumulative doses over a shorter time period because of more frequent dosing that is allowed by self-administration and the safety profile afforded by the sublingual/oral route of administration. For example, during a 17-day dose progression phase for sublingual immunotherapy, a cumulative dose of up to 1610 μg of the allergen can be administered.

TABLE 2

Injection schedule of short ragweed extract to achieve maintenance dose It is recommended that patients receive injection at 5 to 7 day intervals until maintenance dosage based on Units of the major allergen, Amb a 1 (Antigen E) is achieved. Maintenance dosage can be given at 2 to 4 week intervals. [from Direction for Use, Short Ragweed and G. S. Ragweed Mix product package insert, Greer Laboratories, Inc.)

| Dose Number | Vial Concentration | Volume Administered | Dose (Units) |
|---|---|---|---|
| 1 | 0.3 Units/mL | 0.05 mL | 0.015 |
| 2 | 0.3 Units/mL | 0.10 mL | 0.03 |
| 3 | 0.3 Units/mL | 0.20 mL | 0.06 |
| 4 | 0.3 Units/mL | 0.40 mL | 0.12 |
| 5 | 0.3 Units/mL | 0.70 mL | 0.21 |
| 6 | 3.0 Units/mL | 0.10 mL | 0.30 |
| 7 | 3.0 Units/mL | 0.20 mL | 0.60 |
| 8 | 3.0 Units/mL | 0.30 mL | 0.90 |
| 9 | 3.0 Units/mL | 0.50 mL | 1.5 |
| 10 | 3.0 Units/mL | 0.70 mL | 2.1 |
| 11 | 30.0 Units/mL | 0.10 mL | 3.0 |
| 12 | 30.0 Units/mL | 0.15 mL | 4.5 |
| 13 | 30.0 Units/mL | 0.20 mL | 6.0 |
| 14 | 30.0 Units/mL | 0.30 mL | 9.0 |
| 15 | 30.0 Units/mL | 0.40 mL | 12.0 |
| 16 | 30.0 Units/mL | 0.50 mL | 15.0 |
| 17 | 30.0 Units/mL | 0.50 mL | 15.0 |
| 18 | 30.0 Units/mL | 0.50 mL | 15.0 |

Maintenance injection therapy for short ragweed pollen allergen is given at less frequent intervals, typically increasing over a period time to once monthly injections of the highest concentration (30 μg/mL) allergen solution. The maximum doses that can be administered during injection immunotherapy are limited by safety considerations and time available to visit a physician's office to receive the injections. Based on the recommended dose schedule described above and taken from the product package insert, the monthly cumulative maintenance dose of allergen is 15 μg. In contrast, sublingual/oral maintenance immunotherapy allows for monthly cumulative maintenance doses of 6000 μg or 400 times that given by traditional injection immunotherapy.

The present invention, comprising compositions of one or more allergens in amounts that are at least 200 times the injection amounts for the one or more allergens, which are self administered through methods of oral/sublingual routes, are beneficial to patients and also allow for ease of administration of multiple allergens. This is relevant because the induction and maintenance of immunological tolerance requires relatively high allergen doses that are difficult to attain when multiple allergens are included in the immunotherapy formulation.

The dosing intervals may be altered depending on the allergen, the route of administration and the reactions of the patient's immune system. For example, the methods of the present invention may comprise rush or ultra-rush immunotherapy, wherein a more rapid, or rushed, dosing interval is used to reach the maintenance dose of the one or more allergens. During the initial phase of treatment, increasing doses of allergen are given every 30 minutes to a few hours rather than every few days or weeks. Patients may be pre-treated with medications to reduce the risk of an allergic reaction during rush immunotherapy. In an ultra-rush regimen described for injection immunotherapy, the maintenance dose can be reached in 2-3 days by including special precautions in a hospital setting. However, systemic side-effects are observed in 25-75% of patients undergoing this regimen. In contrast, an ultra-rush procedure for sublingual/oral immunotherapy can be given safely over the same 2-3 day time period without the increased risk in inducing systemic side effects. In addition, oral anti-allergy medications such as oral dosage forms of antihistamines, topical corticosteroids, leukotriene inhibitors, or mast cell stabilizers can be administered in the same formulation as the allergen extract.

The present invention comprises methods and compositions for sublingual/oral immunotherapy. Current methods of injection and sublingual/oral allergen immunotherapy comprise giving increasing doses of an allergen to gradually build up a patient's tolerance to the allergen. Incremental doses are enabled by stepwise increases in both the concentration and volume of the allergen composition administered. In sublingual/oral immunotherapy, the allergen extract is given as drops, usually placed under the tongue and then swallowed. Convenience is a benefit of oral immunotherapy because the patient can take the drops at home without the need for a physician or an office visit. In Europe, oral immunotherapy has been successful in treating many types of severe allergies, including those caused by dust mites, pollens, molds, and pets. The oral treatment regimens in Europe follow the same pattern as that of injection regimens, of increasing allergen exposure by using compositions having increasing concentrations of allergens. However, relatively few allergists in the U.S. currently offer oral immunotherapy, as the extracts are not standardized. In addition, the FDA has not approved formulations of any sublingual/oral extract. Those in the U.S. who are currently using allergen extracts in off label usage for oral therapy are also following the same regimen as is used with allergy shots-increasing the allergen dose by providing differing concentrations of allergen compositions.

The present invention comprises methods comprising sublingual/oral administration of a single concentration of allergen compositions and further comprises administration of other agents that may aid in the immunotherapy treatment. For example, patients may be administered immune modulators, such as steroids or antihistamines, in conjunction with administration of the allergen compositions of the present invention. This treatment may occur prior to, during or after the administration of the allergen composition. This immune modulator treatment may stabilize the patient if the patient is in a highly allergic state, may prevent reactions to the allergen composition, or may provide other beneficial aspects to the treatment. For example, adjuvants may be co-administered with the allergen compositions to enhance their immunogenicity or modify their bioavailability. Such co-administration may be in separate compositions or may be present in the allergen composition. Other components included in the allergen compositions of the present invention include, but are not limited to, antihistamines, leukotriene inhibitors, corticosteroids, decongestants, mast-cell stabilizers (cromolyn), beta-receptor agonists, alum, glycolipids, calcium phosphate, surface-active agents, bacterial products, cytokines, hormones, nucleic acids, allergen-specific antibodies, enzymes, IgE-binding agents, acrylic polymers, non-ionic and ionic block copolymers, chitosan, starch, or alginate.

Methods of the present invention comprise providing doses of a single, uniform specific concentration composition. For example, in an oral dosing administration of a liquid composition, the dose comprises one or more drops of a liquid having a specific concentration of one or more allergens. For other dosage formulations, for example, quick dissolving tablets, a dose would be a quick dissolving tablet, and all of the tablets provided would have a uniform or specific concentration of one or more allergens. In an allergen composition, the concentration of one or more allergens does not increase, but remains uniform or constant. An aspect of the methods of the present invention comprises administering a predetermined minimum dose, as delivered by a specified amount of the allergen composition, for a specified time period, such as one or more days, and increasing the dose of the allergen composition by increasing the amount of the composition given to a human or animal until the maximum dose is reached so that immune tolerance is induced and maintained. Induction of immune tolerance comprises the initial administration and any increasing dose amounts until a maximum amount is administered and the human or animal does not have adverse effects. For example, oral doses are provided in increasing amounts of allergen composition until the patient indicates discomfort in the oral cavity or has adverse immune responses to that level of allergen. At that point, the amount of allergen delivered is decreased until no such symptoms are reported or measured. Maintenance immune tolerance levels are attained by providing allergen compositions at a level where the patient does not report adverse or uncomfortable symptoms and a decrease in allergen-specific IgE antibodies or reaction to allergen challenge and an increase in allergen-specific IgG or IgA antibodies or Th2-type cytokine secretion by allergen-specific T cells is measurable.

The present invention comprises a method for immunotherapy, comprising, administering to a human or animal having an allergic response to at least one allergen, one or more drops of a composition comprising a concentration of one or more allergens, and inducing and maintaining immune tolerance to at least one allergen. The allergic response to the at least one allergen is generally measured by skin testing. Inducing and maintaining immune tolerance is generally determined by a reduction in response to the allergen by the human or animal. Such test are known to those skilled in the art. The administering comprises providing a predetermined minimum number of drops on the first day of treatment and increasing the number the drops in the succeeding days until a maximum number of drops is dispensed per day. Alternatively, administering may comprise providing a predetermined minimum number of drops on the first day of treatment and providing the maximum number of drops on each day thereafter. Depending on patient needs, the maximum number of drops may be reduced when environmental exposure to at least one allergen is increased. The drops may be provided by a measured oral dosage device. For the present invention, the dose of allergen for inducing immune tolerance may be from about 100 to about 600 times the dose administered via injection routes. The range of allergen for inducing immune tolerance may be from about 100 to about 500 times the dose administered via injection routes, from about 200 to about 500, from about 300 to about 400, from about 400 times the dose administered via injection routes, and from at least 100 times the dose administered via injection routes, from at least 200 times the dose administered via injection routes, and from at least 400 times the dose administered via injection routes.

Maintaining an immune tolerance is measured by tests known to those skilled in the art such as a measurable decrease in allergen-specific IgE antibodies or reaction to allergen challenge and an increase in allergen-specific IgG or IgA antibodies or Th2-type cytokine secretion by allergen-specific T cells. The compositions of the present invention comprise one or more allergens, including those taught herein, and including compositions wherein the at least one allergen is house dust mite, cat hair, grass pollen, short ragweed pollen, mixtures or combinations thereof.

The present invention comprises methods for manufacture of allergen compositions that are easier to manufacture, less expensive, safer and require less testing to verify concentrations because the compositions are made with specific concentrations of one or more allergens, and that composition does not need to be diluted to provide initial doses for immunotherapy. Additionally, the concentration does not need to be altered to provide for greater concentrations of one or more allergens for later administrations of compositions for maintenance regimens. Thus, the present invention provides methods of making allergen compositions for both initial dose and subsequent doses for immunotherapy, comprising, combining one or more allergens in a predetermined concentration in a pharmaceutical excipient formulation, wherein the concentrations of the allergen compositions are not diluted due to treatment regimen requirements for diluted allergen amounts for the initial doses administered to patients.

The methods of the present invention for administration of the allergen compositions are not limited by the device used to deliver the compositions. Many devices are known in the art that can be used to deliver a known volume of a composition. For example, metered dose devices can be used to administer increasing volumes of a liquid composition so that the amount of allergen delivered to the patient increases with increasing volumes. An ideal device for sublingual/oral delivery consists of a pump system capable of delivering 0.05-1.00 mL of the therapeutic allergen solution and an actuator with an integrated spray or jet-stream insert. Alternatively, droppers can easily dispense the compositions of the present invention. Other routes of administration can employ devices known to those skilled in the art that are capable of delivering exact volumes of the compositions of the present invention.

Compositions of the present invention comprise at least one allergen and pharmaceutical agents or excipients necessary to provide a dosage formulation. Allergens include, but are not limited to those derived from pollens, animal danders, fungi, hymenopteran venoms, insects and housedust mites, plant foods, and animal foods. A particular composition comprises a standardized house dust mite extract (10,000 AU/mL), a standardized grass pollen extract (100,000 BAU/nL) a standardized cat extract (10,000 BAU/mL) and a standardized short ragweed pollen extract (1:20 w/v). Other combinations may depend upon the allergic profile of allergic patients determined by a qualified physician and the identification of specific triggers of the patient's symptoms. Inclusion criteria may be based on allergen skin testing or allergen-specific IgE measurements.

TABLE 3

Representative Allergen Product Formulations

| Allergenic Extract | Vial Concentration | Volume Administered | Dose Delivered |
| --- | --- | --- | --- |
| House Dust Mite | 10,000 AU/mL | 50 μL | 500 AU |
| House Dust Mite | 10,000 AU/mL | 150 μL | 1,500 AU |
| House Dust Mite | 10,000 AU/mL | 1,000 μL | 10,000 AU |
| Cat Hair | 10,000 BAU/mL | 150 μL | 1,500 BAU |
| Grass Pollen | 100,000 BAU/mL | 50 μL | 5,000 BAU |
| Short Ragweed Pollen | 300 U/mL | 200 μL | 60 U/mL |
| Rx 1211[1] | 1,000 BAU/mL | 250 μL | 2,500 BAU |

[1]Rx 1211 represents a patient-specific prescription formulated to contain 1,000 BAU/mL grass pollen, 1,000 AU/mL house dust mite, and 1,000 BAU/mL cat hair extracts. This list is exemplary and the present invention is not limited to the common antigens listed herein, but comprises all antigens that can be provided in a dosage form.

Compositions of the present invention may comprise one or more allergens, including, but not limited to, the allergens listed below along with excipients known to those skilled in the art, and optionally, other pharmaceutical agents such as oral anti-allergy medications such as oral dosage forms of antihistamines, topical corticosteroids, leukotriene inhibitors, or mast cell stabilizers.

TABLE 4

Allergens

Mites

| | |
| --- | --- |
| Mite, House Dust | *Dermatophagoides farinae* |
| Mite, House Dust | *Dermatophagoides pteronyssinus* |
| Mite, Food/Storage | *Acarus siro* |
| Mite, House Dust | *Blomia tropicalis* |
| Mite, Storage | *Chortoglyphus arcuates* |
| Mite, House Dust | *Euroglyphus maynei* |
| Mite, Food/Storage | *Lepidoglyphus destructor* |
| Mite, Food/Storage | *Tyrophagus putrescentiae* |
| Mite, House Dust | *Glycyphagus domesticus* |

Venoms

| | |
| --- | --- |
| Bumble Bee Venom | *Bombus* spp. |
| European Hornet Venom | *Vespa crabro* |
| Honey Bee Venom | *Apis mellifera.* |
| Mixed Hornet Venom | *Dolichovespula* spp |
| Mixed Paper Wasp Venom | *Polistes* spp. |
| Mixed Yellow Jacket Venom | *Vespula* spp. |
| White (bald)-faced Hornet Venom | *Dolichovespula maculate* |
| Yellow Hornet Venom | *Dolichovespula arenaria* |

Insects

| | |
| --- | --- |
| Ant, Carpenter | *Camponotus pennsylvanicus* |
| Ant, Fire | *Solenopsis invicta* |
| Ant, Fire | *Solenopsis richteri* |
| Cockroach, American | *Periplaneta Americana* |
| Cockroach, German | *Blattella germanica* |
| Cockroach, Oriental | *Blatta orientalis* |
| Horse Fly | *Tabanus* spp. |
| House Fly | *Musca domestica* |
| Mayfly | *Ephemeroptera* spp. |
| Mosquito | *Culicidae* sp. |
| Moth | *Heterocera* spp. |

Epithelia, Dander, Hair & Feathers

| | |
| --- | --- |
| Canary Feathers | *Serinus canaria* |
| Cat Epithelia | *Felis catus* (*domesticus*) |
| Cattle Epithelia | *Bos Taurus* |
| Chicken Feathers | *Gallus gallus* (*domesticus*) |
| Dog Epithella, Mixed Breeds | *Canis familiaris* |
| Duck Feathers | *Anas platyrhynchos* |

TABLE 4-continued

Allergens

| | |
|---|---|
| Gerbil Epithelia | *Meriones unguiculatus* |
| Goat Epithelia | *Capra hircus* |
| Goose Feathers | *Anser domesticus* |
| Guinea Pig Epithelia | *Cavia porcellus (cobaya)* |
| Hamster Epithelia | *Mesocricetus auratus* |
| Hog Epithelia | *Sus scrofa* |
| Horse Epithelia | *Equus caballus* |
| Mouse Epithelia | *Mus musculus* |
| Parakeet Feathers | *Psittacidae* spp. |
| Pigeon Feathers | *Columba fasciata* |
| Rabbit Epithelia | *Oryctolagus cuniculus* |
| Rat Spithelia | *Rettus norvegicus* |
| Wool, Sheep | *Ovis aries* |

Dander

| | |
|---|---|
| Cat dander/Antigen | *Felis catus (domesticus)* |
| Dog Dander, Mixed-Breed | *Canis familiaris* |
| Poodle Dander | *Canis familiaris* |

Fungi

| | |
|---|---|
| *Acremonium strictum* | *Cephalosporium acremonium* |
| *Alternaria alternate* | *Alternaria tenuis* |
| *Aspergillus amstelodami* | *Aspergillus glaucus* |
| *Aspergillus flavus* | |
| *Aspergillus furmigatus* | |
| *Aspergillus nidulans* | |
| *Aspergillus niger* | |
| *Aspergillus terreus* | |
| *Aspergillus versicolor* | |
| *Aureobasidium pullulans* | *Pullularia pullulans* |
| *Bipolaris sorokiniana* | *Drechslera sorokiniana, Helminthosporium sativum* |
| *Botrytis cinerea* | |
| *Candida albicans* | |
| *Chaetomium globosum* | |
| *Cladosporium herbarum* | |
| *Cladosporium sphaerospermum* | *Hormodendrum hordei* |
| *Drechslere spicifera* | *Curvularia spicifera* |
| *Epicoccum nigrum* | *Epicoccum purpurascens* |
| *Epidermophyton floccosum* | |
| *Fusarium moniliforme* | |
| *Fusarium solani* | |
| *Geotrichum candidum* | *Oospora lactis* |
| *Gliocladium viride* | *Gliocladium deliquescens* |
| *Helminthosporium solani* | *Spondylocladium atrovirens* |
| *Microsporum canis* | *Microsporum lanosum* |
| *Mucor circinelloides* f. | *Mucor mucedo* |
| *Mucor circinelloides* f. *lusitanicus* | *Mucor racemosus* |
| *Mucor plumbeus* | |
| *Mycogone perniciosa* | |
| *Neurospora intermedia* | *Neurospora sitophila, Monilia sitophila* |
| *Nigrospora oryzae* | |
| *Paecilomyces variotii* | |
| *Penicillium brevi-compactum* | |
| *Penicillium camembertii* | |
| *Penicillium chrysogenum* | |
| *Penicillium digitatum* | |
| *Penicillium expensum* | |
| *Penicillium notatum* | |
| *Penicillium roquefortii* | |
| *Phoma betae* | |
| *Phomma herbarum* | *Phoma pigmentivora* |
| *Rhigopus oryzae* | *Rhizopus arrhizus* |
| *Rhizopus stolonifer* | *Rhizopus nigricans* |
| *Rhodotorula mucilaginosa* | *Rhodotorula rubra* var. *mucilaginosa* |
| *Saccharomyces cerevisiae* | |
| *Scopulariopsis brevicaulis* | |
| *Serpula lacrymans* | *Merulius lacrymans* |
| *Setosphaeria rostrata* | *Exserohilum rostratum, Helminthosporium halodes* |
| *Stemphylium botryosum* | |
| *Stemphylium solani* | |
| *Trichoderma harzianum* | *Trichoderma viride* |
| *Trichophyton mentagrophytes* | *Trichophyton interdigitale* |
| *Trichophyton rubrum* | |
| *Trichothecium roseum* | *Cephalothecium roseum* |

Smuts

| | |
|---|---|
| Barley Smut | *Ustilago nuda* |
| Bermuda Grass Smut | *ustilago cynodontis* |
| Corn Smut | *Ustilago maydis* |
| Johnson Grass Smut | *Sporisorium cruentum* |
| Oat Smut | *Ustilago avenae* |
| Wheat Smut | *Ustilago tritici* |

Grass Pollens

| | |
|---|---|
| Bahia | *Paspalum notatum* |
| Bermuda | *Cynodon dactylon* |
| Blue, Canada | *Poa compressa* |
| Brome, Smooth | *Bromus inermis* |

TABLE 4-continued

| Allergens | |
|---|---|
| Canary | *Phalaris arundinacea* |
| Corn | *Zea mays* |
| Couch/Quack | *Elytrigia repens* (*Agropyron repens*) |
| Johnson | *Sorghum halepense* |
| Kentucky Blue | *Poa pratensis* |
| Meadow Fescue | *Festuca pratensis* (*elatior*) |
| Oat, Cultivated | *Avena sativa* |
| Orchard | *Dactylis glomerata* |
| Red Top | *Agrostis gigantean* (*alba*) |
| Rye, Cultivated | *Secale cereale* |
| Rye, Giant Wild | *Leymus* (*Elymus*) *condensatus* |
| Rye, Italian | *Lolium perenne* ssp. *multiflorum* |
| Rye, Perennial | *Lolium perenne* |
| Sweet Vernal | *Anthoxanehum odoratum* |
| Timothy | *Phleum pratense* |
| Velvet | *Holcus lanatus* |
| Wheat, Cultivated | *Triticum aestivum* |
| Wheatgrass, Western | *Elymus* (*Agropyron*) *smithii* |
| Weed Pollens | |
| *Allscale* | *Atriplex polycarpa* |
| *Baccharis* | *Baccharis halimifolia* |
| *Baccharis* | *Baccharis sarothroides* |
| Burrobrush | *Hymenoclea salsola* |
| Careless Weed | *Amaranthus hybridus* |
| Cocklebur | *Xanthium strumarium* (*commune*) |
| Dock, Yellow | *Rumex crispus* |
| Dog Fennel | *Eupatorium capillifolium* |
| Goldenrod | *Solidago* spp. |
| Hemp, Western Water | *Amaranthus tuberculatus* (*Acnida tamariscina*) |
| Iodine Bush | *Allenrolfea occidentalis* |
| Jerusalem Oak | *Chenopodium botrys* |
| Kochia/Firebush | *Kochia scoparia* |
| Lambs Quarter | *Chenopodium album* |
| Marsh Elder, Burweed | *Iva xanthifolia* |
| Marsh Elder, Narrowleaf | *Iva angustifolia* |
| Marsh Elder, Rough | *Iva annua* (*ciliata*) |
| Mexican Tea | *Chenopodium ambrosioides* |
| Mugwort, Common | *Artemisia vulgaris* |
| Mugwort, Darkleaved | *Artemisia ludoviciana* |
| Nettle | *Urtica dioica* |

TABLE 4-continued

| Allergens | |
|---|---|
| Palmer's Amaranth | *Amaranthus palmeri* |
| Pigweed, Redroot/Rough | *Amaranthus retroflexus* |
| Pigweed, Spiny | *Amaranthus spinosus* |
| Plantain, English | *Plantago lanceolata* |
| Poverty Weed | *Iva axillaris* |
| Quailbrush | *Atriplex lentiformis* |
| Rabbit Bush | *Ambrosia deltoidea* |
| Ragweed, Desert | *Ambrosia dumosa* |
| Ragweed, False | *Ambrosia acanthicarpa* |
| Ragweed, Giant | *Ambrosia trifida* |
| Ragweed, Short | *Ambrosia artemisiifolia* |
| Ragweed, Slender | *Ambrosia confertiflora* |
| Ragweed, Southern | *Ambrosia bidentata* |
| Ragweed, Western | *Ambrosia psilostachya* |
| Russian Thistle | *Salsola kali* (*pestifer*) |
| Sage, Coastal | *Artemisia californica* |
| Sage, Pasture | *Artemisia frigida* |
| Sagebrush, Common | *Artemisia tridentate* |
| Saltbush, Annual | *Atriplex wrightii* |
| Shadscale | *Atriplex confertifolia* |
| Sorrel, Red/Sheep | *Rumex acetosella* |
| Wingscale | *Atriplex canescens* |
| Wormwood, Annual | *Artemisia annua* |
| Tree Pollens | |
| *Acacia* | *Acacia* spp. |
| Alder, European | *Alnus glutinosa* |
| Alder, Red | *Alnus rubra* |
| Alder, Tag | *Alnus incana* ssp. *rugosa* |
| Alder, White | *Alnus rhombifolia* |
| Ash, Arizona | *Fraxinus velutina* |
| Ash, Green/Red | *Fraxinus pennsylvanica* |
| Ash, Oregon | *Fraxinus latifolia* |
| Ash, White | *Fraxinus americana* |
| Aspen | *Populus tremuloides* |
| Bayberry | *Myrica cerifera* |
| Beech, American | *Fagus grandifolia* (*americana*) |
| Beefwood/Australian Pine | *Casuarina equisetifolia* |
| Birch, Black/Sweet | *Betula lenta* |
| Birch, European White | *Betula pendula* |
| Birch, Red/River | *Betula nigra* |
| Birch, Spring | *Betula occidentalis* (*fontinalis*) |
| Birch, White | *Betula populifolia* |

TABLE 4-continued

| Allergens | |
|---|---|
| Box Elder | *Acer negundo* |
| Cedar, Japanese | *Cryptomeria japonica* |
| Cedar, Mountain | *Juniperus ashei (sabinoides)* |
| Cedar, Red | *Juniperus virginiana* |
| Cedar, Salt | *Tamarix gallica* |
| Cottonwood, Black | *Populus balsamifera* ssp. *trichocarpa* |
| Cottonwood, Eastern | *Populus deltoides* |
| Cottonwood, Fremont | *Populus fremontii* |
| Cottonwood, Rio Grande | *Populus wislizeni* |
| Cottonwood, Western | *Populus monilifera (sargentii)* |
| Cypress, Arizona | *Cupressus arizonica* |
| Cypress, Bald | *Taxodium distichum* |
| Cypress, Italian | *Cupressus sempervirens* |
| Elm, American | *Ulmus americana* |
| Elm, Cedar | *Ulmus crassifolia* |
| Elm, Siberian | *Ulmus pumila* |
| Eucalyptus | *Eucalyptus globulus* |
| Hackberry | *Celtis occidentalis* |
| Hazelnut | *Corylus americana* |
| Hazelnut, European | *Corylus avellana* |
| Hickory, Pignut | *Carya glabra* |
| Hickory, Shagbark | *Carya ovata* |
| Hickory, Shellbark | *Carya laciniosa* |
| Hickory, White | *Carya alba* |
| Juniper, Oneseed | *Juniperus monosperma* |
| Juniper, Pinchot | *Juniperus pinchotii* |
| Juniper, Rocky Mountain | *Juniperus scopulorum* |
| Juniper, Utah | *Juniperus osteosperma* |
| Juniper, Western | *Juniperus occidentalis* |
| Locust Blossom, Black | *Robinia pseudoacacia* |
| Mango Blossom | *Mangifera indica* |
| Maple, Coast | *Acer macrophyllum* |
| Maple, Red | *Acer rubrum* |
| Maple, Silver | *Acer saccharinum* |
| Maple, Sugar | *Acer saccharum* |
| Melaleuca | *Melaleuca quinquenervia (leucadendron)* |
| Mesquite | *Prosopis glandulosa (julifiora)* |
| Mulberry, Paper | *Broussonetia papyrifera* |
| Mulberry, Red | *Morus rubra* |
| Mulberry, White | *Morus alba* |
| Oak, Arizona/Gambel | *Quercus gambeiji* |
| Oak, Black | *Quercus velutina* |
| Oak, Bur | *Quercus macrocarpa* |
| Oak, California Black | *Quercus kelloggii* |
| Oak, California Live | *Quercus agrifolia* |
| Oak, California White/Valley | *Quercus lobata* |
| Oak, English | *Quercus robur* |
| Oak, Holly | *Quercus ilex* |
| Oak, Post | *Quercus stellata* |
| Oak, Red | *Quercus rubra* |
| Oak, Scrub | *Quercus dumosa* |
| Oak, Virginia Live | *Quercus virginiana* |
| Oak, Water | *Quercus nigra* |
| Oak, Western White/Gany | *Quercus garryana* |
| Oak, White | *Quercus alba* |
| Olive | *Olea europaea* |
| Olive, Russian | *Elaeagnus angustifolia* |
| Orange Pollen | *Citrus sinensis* |
| Palm, Queen | *Arecastrum romanzoffianum (Cocos plumosa)* |
| Pecan | *Carya illinoensis* |
| Pepper Tree | *Schinus molle* |
| Pepper Tree/Florida Holly | *Schinus terebinthifolius* |
| Pine, Loblolly | *Pinus taeda* |
| Pine, Eastern White | *Pinus strobus* |
| Pine, Longleaf | *Pinus palustris* |
| Pine, Ponderosa | *Pinus ponderosa* |
| Pine, Slash | *Pinus elliottii* |
| Pine, Virginia | *Pinus virginiana* |
| Pine, Western White | *Pinus monticola* |
| Pine, Yellow | *Pinus echinata* |
| Poplar, Lombardy | *Populus nigra* |
| Poplar, White | *Populus alba* |
| Privet | *Ligustrum vulgare* |
| Sweet Gum | *Liquidambar styraciflua* |
| Sycamore, Eastern | *Platanus occidentalis* |
| Sycamore, Oriental | *Platanus orientalis* |
| Sycamore, Western | *Platanus racemosa* |
| Sycamore/London Plane | *Platanus acerifolia* |
| Walnut, Black | *Juglans nigra* |
| Walnut, California Black | *Juglans californica* |
| Walnut, English | *Juglans regia* |
| Willow, Arroyo | *Salix lasiolepis* |
| Willow, Black | *Salix nigra* |
| Willow, Pussy | *Salix discolor* |
| Flowers: Wild & Cultivated | |
| Daisy, Ox-Eye | *Chrysanthemum leucanthemum* |
| Dandelion | *Taraxacum officinale* |
| Sunflower | *Helianthus annuus* |

TABLE 4-continued

| Allergens | |
|---|---|
| Cultivated Farm Plant Pollens | |
| Alfalfa | *Medicago sativa* |
| Castor Bean | *Ricinus communis* |
| Clover, Red | *Trifolium pratense* |
| Mustard | *Brassica* spp. |
| Sugar Beet | *Beta vulgaris* |
| Plant Food | |
| Almond | *Prunus dulcis* |
| Apple | *Malus pumila* |
| Apricot | *Prunus armeniaca* |
| Banana | *Musa paradisiaca (sapientum)* |
| Barley | *Hordeum vulgare* |
| Bean, Lima | *Phaseolus lunatus* |
| Bean, Navy | *Phaseolus vulgaris* |
| Bean, Pinto | *Phaseolus* sp. |
| Bean, Red Kidney | *Phaseolus* sp. |
| Bean, String/Green | *Phaseolus vulgaris* |
| Blackberry | *Rubus allegheniensis* |
| Blueberry | *Vaccinium* sp. |
| Broccoli | *Brassica oleracea* var. *botrytis* |
| Buckwheat | *Fagopyrum esculentum* |
| Cabbage | *Brassica oleracea* var. *capitata* |
| Cacao Bean | *Theobroma cacao* |
| Cantaloupe | *Cucumis melo* |
| Carrot | *Daucus carota* |
| Cauliflower | *Brassica oleracea* var. *botrytis* |
| Celery | *Apium graveolens* var. *dulce* |
| Cherry | *Prunus* sp. |
| Cinnamon | *Cinnamomum verum* |
| Coffee | *Coffee arabica* |
| Corn | *Zea mays* |
| Cranberry | *Vaccinium macrocarpon* |
| Cucumber | *Cucumis sativus* |
| Garlic | *Allium sativum* |
| Ginger | *Zingiber officinale* |
| Grape | *Vitis* sp. |
| Grapefruit | *Citrus paradisi* |
| Hops | *Humulus lupulus* |
| Lemon | *Citrus limon* |
| Lettuce | *Lactuca sativa* |
| Malt | |
| Mushroom | *Agaricus campestris* |
| Mustard | *Brassica* sp. |
| Nutmeg | *Myristica fragrans* |
| Oat | *Avena sativa* |
| Olive, Green | *Olea europaea* |
| Onion | *Allium cepa* var. *cepa* |
| Orange | *Citrus sinensis* |
| Pea, Blackeye | *Vigna unguiculata* |
| Pea, Green (English) | *Pisum sativum* |
| Peach | *Prunus persica* |
| Pear | *Pyrus communis* |
| Pepper, Black | *Piper nigrum* |
| Pepper, Green | *Capsicum annuum* var. *annuum* |
| Pineapple | *Ananas comosus* |
| Potato, Sweet | *Ipomoea batatas* |
| Potato, White | *Solanum tuberosum* |
| Raspberry | *Rubus idaeus* var. *idaeus* |
| Rice | *Oryza sativa* |
| Rye | *Secale cereale* |
| Sesame Seed | *Sesamum orientale (indicum)* |
| Soybean | *Glycine max* |
| Spinach | *Spinacia oleracea* |
| Squash, Yellow | *Cucurbita pepo* var. *melopepo* |
| Strawberry | *Fragaria chiloensis* |
| Tomato | *Lycopersicon esculentum (lycopersicum)* |
| Turnip | *Brassica rapa* var. *rapa* |
| *Vanilla* Bean | *Vanilla planifolia* |
| Watermelon | *Citrullus lanatus* var. *lanatus* |
| Wheat, Whole | *Triticum aestivum* |
| Fish & Shellfish | |
| Bass, Black | *Micropterus* sp. |
| Catfish | *Ictalurus punctatus* |
| Clam | *Mercenaria mercenaria* |
| Codfish | *Gadus morhua* |
| Crab | *Callinectes sapidus* |
| Flounder | *Platichthys* sp. |
| Halibut | *Hippoglossus* sp. |
| Lobster | *Homarus americanus* |
| Mackerel | *Scomber scombrus* |
| Oyster | *Crassostrea virginica* |
| Perch | *Sebastes marinus* |
| Salmon | *Salmo salar* |
| Sardine | *Clupeiformes* |
| Scallop | *Pectan magellanicus* |
| Shrimp | *Penaeus* sp. |
| Trout, Lake | *Salvelinus* sp. |
| Tuna Fish | *Thunnus* sp. |
| Animal Foods | |
| Beef | *Bos taurus* |
| Lamb | *Ovis aries* |
| Pork | *Sus scrofa* |

TABLE 4-continued

Allergens

Poultry Products

| | |
|---|---|
| Chicken | *Gallus gallus* |
| Egg, Chicken, White | *Gallus gallus* |
| Egg, Chicken, Yolk | *Gallus gallus* |
| Turkey | *Meleagris gallopavo* |

Dairy Products

| | |
|---|---|
| Casein, bovine | *Bos taurus* |
| Milk, bovine | *Bos taurus* |

Nuts

| | |
|---|---|
| Brazil Nut | *Bertholletia excelsa* |
| Cashew Nut | *Anacardium occidentale* |
| Coconut | *Cocos nucifera* |
| Filbert/Hazelnut | *Corylus americana* |
| Peanut | *Arachis hypogaea* |
| Pecan | *Carya illinoensis* |
| Walnut, Black | *Juglans nigra* |
| Walnut, English | *Juglans regia* |

Miscellaneous

Latex

The precise mechanisms by which allergen immunotherapy achieves clinical efficacy is still not completely known, but successful treatment is usually accompanied by a decrease in allergen sensitivity as measured by a decrease in symptom and medication scores, and reductions in allergen-specific IgE antibodies, lessened reactions to skin test or other provocative allergen challenge and lessened allergen-induced IL-4 and IL-5 cytokine secretion with a concomitant increase in allergen-specific IgG or IgA antibodies, and IFN (interferon)-gamma secretion by allergen-specific T cells. Methods of the present invention comprise oral administration to a human or animal subject of an effective amount of a composition comprising at least one allergen to which the human or animal has shown a measurable immune response, wherein the composition is provided over an interval of time until the subject has a measurable decrease in allergen-specific IgE antibodies or reaction to allergen challenge and an increase in allergen-specific IgG or IgA antibodies or Th2-type cytokine secretion by allergen-specific T cells.

The present invention comprises compositions for delivery of antigens to a human or animal. Such compositions comprise any dosage form including liquids, creams, tablets, fast-dissolve tablets, capsules, time-release dosage formulations, inhalants, nanoparticles and other dosage forms known to those of skill in the art. The composition is provided to the human or animal in a single concentration of one or more antigens, and the amount of antigen is increased by increasing the number of units of the single concentration provided to the human or animal.

All patents, patent applications and references included herein are specifically incorporated by reference in their entireties.

It should be understood, of course, that the foregoing relates only to preferred embodiments of the present invention and that numerous modifications or alterations may be made therein without departing from the spirit and the scope of the invention as set forth in this disclosure.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

A patient with seasonal allergic rhinitis with a history of ocular and nasal symptoms during the months of September-November and sensitivity to short ragweed pollen extract by skin testing elects to be treated using sublingual/oral immunotherapy. The standard treatment regimen as outlined in Bowen (2004) consists of a build up phase using drops (approximately 10-, 100-, and 300 Amb a 1 Units/mL concentrations; see Table 5. Doses are escalated until the patient reaches a daily dose of 100-300 Amb a 1 Units. Maintenance therapy at this dose is continued through the pollen season during which the patient's sensitivity decreases as measured by objective measures of symptoms and medication intake.

TABLE 5

SLIT schedule of short ragweed extract to achieve maintenance dose During a 17-day dose progression phase, patients receive a daily dose of 0.5-300 Amb a 1 Units as drops (10-, 100-, and 300 IR/ml concentrations). Doses are escalated until patients reach a daily dose of at least 100 IR (116 U/mL), with an objective of reaching 300 IR daily in maintenance therapy. [from Bowen et al. 2004. Ann Allergy Asthma Immunol 93: 425-430.]

| Phase | Vial Concentration[1] | Volume Administered | Dose (Units) |
|---|---|---|---|
| Dose progression Phase | | | |
| Day 1 | 10 | 0.05 mL | 0.5 |
| Day 2 | 10 | 0.15 mL | 1.5 |
| Day 3 | 10 | 0.30 mL | 3.0 |
| Day 4 | 10 | 0.50 mL | 5.0 |
| Day 5 | 100 | 0.05 mL | 5.0 |
| Day 6 | 100 | 0.15 mL | 15.0 |
| Day 7 | 100 | 0.30 mL | 30.0 |
| Day 8 | 100 | 0.50 mL | 50.0 |
| Day 9 | 300 | 0.05 mL | 15.0 |
| Day 10 | 300 | 0.15 mL | 45.0 |
| Day 11 | 300 | 0.30 mL | 90.0 |
| Day 12 | 300 | 0.50 mL | 150 |
| Day 13 | 300 | 0.60 mL | 180 |
| Day 14 | 300 | 0.70 mL | 210 |
| Day 15 | 300 | 0.80 mL | 240 |
| Day 16 | 300 | 0.90 mL | 270 |
| Day 17 | 300 | 1.00 mL | 300 |
| Maintenance Phase | | | |
| Daily throughout pollen season | 300 | 1.00 mL | 300 |

[1]Concentrations and doses converted to Amb a 1 U/mL based on 1 IR = 1 Amb a 1 U.
[2]Volume based on 1 drop = 50 μL The present invention allows for a significant simplification of the dose regimen; see Table 6: As is the case with the standard treatment, the patient reaches a daily dose of 100-300 Amb a 1 Units; however the build up phase is accelerated and only a single concentration of short ragweed vaccine is used.

TABLE 6

Sublingual/Oral dosage schedule to achieve maintenance dose
Daily doses of 0.05 mL is given for 2 weeks, followed by daily doses
of 0.15 mL of the same concentration for maintenance dosing.

| Phase | Vial Concentration[1] | Volume Administered | Dose (Units) |
|---|---|---|---|
| Dose progression Phase | | | |
| Day 1 | 300 | 0.05 mL | 15.0 |
| Day 2 | 300 | 0.15 mL | 45.0 |
| Day 3 | 300 | 0.30 mL | 90.0 |
| Day 4 | 300 | 0.50 mL | 150 |
| Day 5 | 300 | 0.60 mL | 180 |
| Day 6 | 300 | 0.70 mL | 210 |
| Day 7 | 300 | 0.80 mL | 240 |
| Day 8 | 300 | 0.90 mL | 270 |
| Day 9 | 300 | 1.00 mL | 300 |
| Maintenance Phase | | | |
| Daily throughout pollen season | 300 | 1.00 mL | 300 |

[1]Concentrations and doses converted to Amb a 1 U/mL based on 1 IR = 1 Amb a 1 U.
[2]Volume administered in precise metered volumes.

Example 2

A patient with perennial rhinitis with a history of cat-allergy and associated skin test reactivity to cat extract is treated using the following sublingual/oral dose regimen. Daily doses of 50 μL of a standardized cat extract (10,000 BAU/mL) for 2 weeks, followed by daily doses of 150 μL of the same formulation for 2 weeks. After this initial desensitization step, the patient initiates a maintenance regimen of weekly doses of 150 μL of a standardized cat extract (10,000 BAU/mL); see Table 7. During the maintenance phase of treatment, the patient is able to tolerate the presence of cats and the patient's sensitivity decreases as measured by objective measures of symptoms and medication intake. Provocation challenge tests also show significant reduction in sensitivity cat allergens. Specific cytokine analysis in mucosal secretions shows reduction in Th2-associated responses.

TABLE 7

Sublingual/Oral dosage schedule to achieve maintenance dose
Daily doses of 0.05 mL is given for 2 weeks, followed by daily doses
of 0.15 mL of the same concentration for 2 weeks. Maintenance
dosing is administered at less frequent intervals e.g. once a week.
[from Example 1 in provisional patent application]

| Phase | Vial Concentration | Volume Administered | Dose (BAU) |
|---|---|---|---|
| Desensitization Phase | | | |
| Days 1-14 | 10,000 BAU/mL | 0.05 mL | 500 |
| Days 15-30 | 10,000 BAU/mL | 0.15 mL | 1500 |
| Maintenance Phase | 10,000 BAU/mL | 0.15 mL | 1500 |

Example 3

A patient with perennial rhinitis mild asthma with a documented history and sensitivity to house dust mites, grass and short ragweed pollen extract is treated with the methods of the present invention. The patient had initiated conventional injection allergen immunotherapy with success, but has difficulty complying with the maintenance injection schedule due to the significant travel distance to the physician's office. The patient undergoes an accelerated (i.e. "rush") sublingual/oral dose regimen at the physician's office involving five sequential 50 μL doses, spaced 30 minutes apart, of a therapeutic mixture containing 1,000 AU/mL standardized house dust mite extract, 1,000 BAU/mL standardized grass pollen extract and 1:20 w/v short ragweed pollen. The patient tolerates the cumulative 250 μL dose of the therapeutic formulation. The patient initiates a maintenance program of weekly 250 μL sublingual/oral doses; see Table 8. Treatment compliance is no longer an issue and all of the therapeutic benefits achieved with the prior injection immunotherapy treatment is maintained during the course of the new treatment regimen.

TABLE 8

Sublingual/Oral dosage schedule to achieve maintenance dose
Rush buildup is achieved in 2 days starting with pre-medications
(H1 antagonist, H2 antagonist and corticosteroids) begun on day 0.
Five sequential 0.05 mL doses of the maintenance concentrate
(1,000 AU/mL mite extract, 1,000 BAU/mL grass pollen extract, and
1:20 w/v ragweed pollen extract), spaced 30 minutes apart are given
on day 1, followed by daily 0.25 mL of the maintenance concentrate.
[from Example 3 in provisional patent application]

| Phase | Vial Concentration[1] | Volume Administered | Dose (BAU) |
|---|---|---|---|
| Rush buildup Phase | | | |
| Dose 1 | 1,000 BAU/mL | 0.05 mL | 50 BAU |
| Dose 2 | 1,000 BAU/mL | 0.05 mL | 50 BAU |
| Dose 3 | 1,000 BAU/mL | 0.05 mL | 50 BAU |
| Dose 4 | 1,000 BAU/mL | 0.05 mL | 50 BAU |
| Dose 5 | 1,000 BAU/mL | 0.05 mL | 50 BAU |
| Maintenance Phase | 1,000 BAU/mL | 0.25 mL | 2,500 BAU |

[1]A single concentration (maintenance concentrate) is used for buildup and maintenance phases of the treatment (=1,000 AU/mL mite extract; 1,000 BAU/mL grass pollen extract; 1:20 w/v ragweed pollen extract).

Example 4

A patient with allergic rhinitis and asthma with symptoms induced by multiple allergens including grass pollens, house dust mites, and cat hair is prescribed sublingual/oral immunotherapy. The buildup phase is initiated using 50 μL of an allergen formulation containing 1,000 BAU/mL standardized grass pollen extract, 1,000 AU/mL standardized house dust mite extract and 1,000 BAU/mL standardized cat extract. The patient complains of oral-mucosal itching within a hour after administering the allergen formulation. The patient is given 10 mg of Cetirizine to treat the side-effect and the allergen formulation is re-formulated to include 200 mg/mL Cetirizine in order to co-administer 10 mg of the antihistamine in the 50 μL dose volume. The patient no longer experiences the oral-mucosal itching after taking the doses. The maintenance dose is initiated two weeks later using 150 μL of the allergen formulation with 67 mg/mL Cetirizine or alternatively, without the antihistamine.

LIST OF REFERENCES

1. Package Insert. Allergenic Extracts: Short Ragweed and G. S. Ragweed Mix—Suggested Dosage Schedule and Instructions. Greer Laboratories, Inc., Lenoir N.C.
2. Staloral: Package Leaflet for Patient. Stallergenes, Antony, France.

What is claimed is:
1. A method for immunotherapy, comprising,
administering to oral mucosa of a human, having an allergic response to at least one allergen, a first dose of a composition comprising a single concentration of the at least one allergen; wherein the at least one allergen is AMB a 1, house dust mite extract, cat hair extract, grass pollen extract, short ragweed pollen extract, or combinations thereof; wherein the at least one allergen is provided at a dose of at least 15 units of AMB a 1, 500 BAU of cat hair extract, 1000 AU of dust mite extract, 1000 BAU of grass pollen extract, 1:20 w/v of short ragweed pollen extract, or combinations thereof; wherein the dose of the at least one allergen does not exceed an amount that causes discomfort or adverse immune responses (maximum tolerable dose); and wherein a portion of the first dose is absorbed by the oral mucosa;

administering to the oral mucosa of the human having the allergic response to the at least one allergen, one or more subsequent doses of the composition comprising a single concentration of the at least one allergen; wherein the volume of the one or more subsequent doses are larger than the first dose; wherein the first dose and each of the one or more subsequent doses are administered at the same concentration; wherein a portion of the subsequent dose is absorbed by the oral mucosa; and wherein the subsequent dose of the at least one allergen does not exceed an amount that causes discomfort or adverse immune responses; and inducing a decrease in the allergic response of the human to the at least one allergen.

2. The method of claim 1, wherein the allergic response to the at least one allergen is measured by skin testing.

3. The method of claim 1, wherein inducing a decrease in the allergic response of the human to the at least one allergen comprises a change in an immunological response to the at least one allergen by the human, wherein a decrease in the immunological response is indicated by a decrease in allergen-specific IgE antibodies, a decrease in the reaction of the human to allergen challenge, an increase in allergen-specific IgG antibodies, an increase in allergen-specific IgA antibodies, or a decrease in Th2-type cytokine secretion by allergen-specific T cells.

4. The method of claim 1, wherein the administration of the subsequent dose comprises providing an increased dosage as compared to the first dose in succeeding days until a maximum tolerable dosage is dispensed per day.

5. The method of claim 1, wherein the administration of the first dose occurs on the first day of treatment and the administration of the subsequent dose comprises providing a maximum immune tolerable dosage on each day thereafter.

6. The method of claim 5, wherein the maximum tolerable dosage is reduced when environmental exposure of the human to the at least one allergen is increased.

7. The method of claim 4, wherein the maximum tolerable dosage is reduced when environmental exposure of the human to the at least one allergen is increased.

8. The method of claim 1, wherein the dose of the at least one allergen for inducing a decrease in the allergic response is greater than a dose that would be required to induce a similar change in the allergic response administered by injection immunotherapy.

9. The method of claim 1, further comprising maintaining a decrease in the allergic response of the human to the at least one allergen.

10. The method of claim 9, wherein the maintenance is indicated by a continued decrease in allergen-specific IgE antibodies, a continued decrease in the reaction to allergen challenge, a continued increase in allergen-specific IgG antibodies, a continued increase in allergen-specific IgA antibodies, or a continued decrease in Th2-type cytokine secretion by allergen-specific T cells.

11. The method of claim 9, wherein maintaining a decrease in the allergic response of the human to the at least one allergen comprises providing a maximum tolerable dose per day.

12. The method of claim 11, wherein the maximum tolerable dose is reduced when environmental exposure of the human to the at least one allergen is increased.

13. The method of claim 9, wherein the dose of the at least one allergen for maintaining a decrease in the allergic response of the human to the at least one allergen is greater than a similar dose that would be required for maintaining a change in the allergic response of the human to the at least one allergen administered by injection immunotherapy.

14. The method of claim 1, wherein the first dose is given on a first day and the subsequent dose is given on a second day.

15. The method of claim 1, wherein the first dose and the subsequent dose are given on the same day.

16. The method of claim 9, wherein the maintenance of a decrease in the allergic response of the human to the at least one allergen occurs in less than 21 days from the day of administration of the first dose.

17. The method of claim 1, wherein the composition is a liquid.

18. The method of claim 17, wherein the liquid composition is provided by a metered oral dosage device that is capable of administering the liquid composition in drop form, and optionally, in a dose comprising 0.05 ml to 1.00 ml.

* * * * *